(12) United States Patent
Miyasato et al.

(10) Patent No.: US 9,899,704 B2
(45) Date of Patent: Feb. 20, 2018

(54) NON-AQUEOUS ELECTROLYTE SOLUTION FOR BATTERY AND LITHIUM SECONDARY BATTERY

(71) Applicant: Mitsui Chemicals, Inc., Minato-ku, Tokyo (JP)

(72) Inventors: Masataka Miyasato, Sodegaura (JP); Satoko Fujiyama, Kisarazu (JP); Takashi Hayashi, Ichihara (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 0 days.

(21) Appl. No.: 14/915,550

(22) PCT Filed: Sep. 17, 2014

(86) PCT No.: PCT/JP2014/074585
§ 371 (c)(1),
(2) Date: Feb. 29, 2016

(87) PCT Pub. No.: WO2015/045989
PCT Pub. Date: Apr. 2, 2015

(65) Prior Publication Data
US 2016/0211551 A1 Jul. 21, 2016

(30) Foreign Application Priority Data
Sep. 25, 2013 (JP) .................. 2013-198670

(51) Int. Cl.
*H01M 10/0567* (2010.01)
*H01M 10/0525* (2010.01)
(Continued)

(52) U.S. Cl.
CPC ...... *H01M 10/0567* (2013.01); *C07D 327/10* (2013.01); *H01M 10/052* (2013.01);
(Continued)

(58) Field of Classification Search
CPC ......... H01M 10/0525; H01M 10/0567; H01M 10/0568; H01M 10/0569
See application file for complete search history.

(56) References Cited

U.S. PATENT DOCUMENTS 7,799,470 B2 * 9/2010 Cho .................. H01M 10/0525
429/199
2006/0172201 A1 * 8/2006 Yasukawa ............. H01M 4/133
429/329
(Continued)

FOREIGN PATENT DOCUMENTS

| CN | 101371397 A | 2/2009 |
| CN | 103098290 A | 5/2013 |

(Continued)

OTHER PUBLICATIONS

International Search Report (PCT/ISA/210) dated Nov. 18, 2014, by the Japanese Patent Office as the International Searching Authority for International Application No. PCT/JP2014/074585.
(Continued)

*Primary Examiner* — Anca Eoff
(74) *Attorney, Agent, or Firm* — Buchanan, Ingersoll & Rooney PC

(57) ABSTRACT

A non-aqueous electrolyte solution for a battery includes: an additive A which is a compound represented by formula (I); and an additive B which is at least one selected from the group consisting of an aromatic compound having at least one of a halogen atom or an alkyl group and a carbamate, and which is a compound other than carbonates or a cyclic sulfates. In formula (I), $R^1$ represents a group represented by formula (II) or a group represented by formula (III) and $R^2$ represents H, a C1-6 alkyl group, a group represented by formula (II), or a group represented by formula (III); or $R^1$ and $R^2$ represent groups which combine to form a benzene ring or cyclohexyl ring. In formula (II), $R^3$ represents a halogen atom, a C1-6 alkyl group, a C1-6 alkyl halide group, a C1-6 alkoxy group, or a group represented by formula (IV).

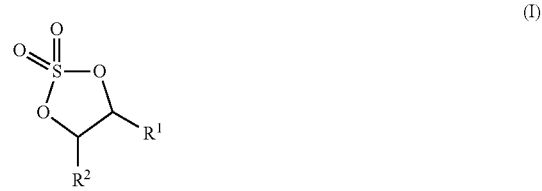

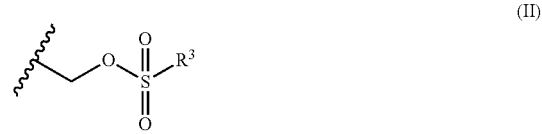

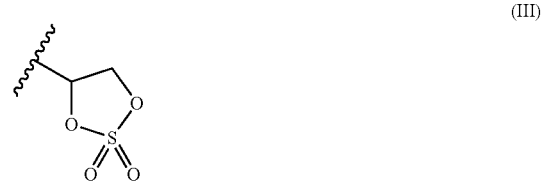

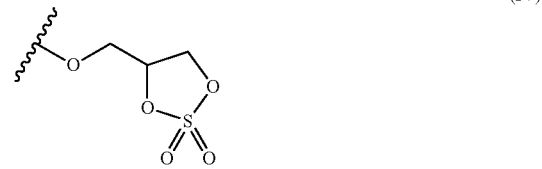

10 Claims, 1 Drawing Sheet

(51) Int. Cl.
*C07D 327/10* (2006.01)
*H01M 10/052* (2010.01)

(52) U.S. Cl.
CPC ............ *H01M 10/0525* (2013.01); *H01M 2300/0025* (2013.01); *Y02T 10/7011* (2013.01)

(56) References Cited

U.S. PATENT DOCUMENTS

| | | |
|---|---|---|
| 2010/0018034 A1 | 1/2010 | Miyasaka et al. |
| 2013/0171514 A1 | 7/2013 | Mio et al. |

FOREIGN PATENT DOCUMENTS

| | | |
|---|---|---|
| JP | 2003-308875 A | 10/2003 |
| JP | 2006-140115 A | 6/2006 |
| JP | 2010-251313 A | 11/2010 |
| KR | 10-2004-0092425 A | 11/2004 |
| KR | 10-2013-0043221 A | 4/2013 |
| WO | WO 2008/032657 A1 | 3/2008 |
| WO | WO 2012/053644 A1 | 4/2012 |
| WO | WO 2013/058387 A1 | 4/2013 |

OTHER PUBLICATIONS

Written Opinion (PCT/ISA/237) dated Nov. 18, 2014, by the Japanese Patent Office as the International Searching Authority for International Application No. PCT/JP2014/074585.

First Notice of Opinion of Examination issued by the State Intellectual Property Office of People's Republic of China in corresponding Chinese Patent Application No. 201480045534.4 dated Apr. 6, 2017 (14 pages including partial English translation).

Extended Search Report issued by the European Patent Office in corresponding European Patent Application No. 14849274.7 dated Mar. 17, 2017 (7 pages).

Notice for Submission of Opinions issued by the Korean Intellectual Property Office in corresponding Korean Patent Application No. 10-2016-7004039 dated Jun. 1, 2017 (14 pages including partial English translation).

\* cited by examiner

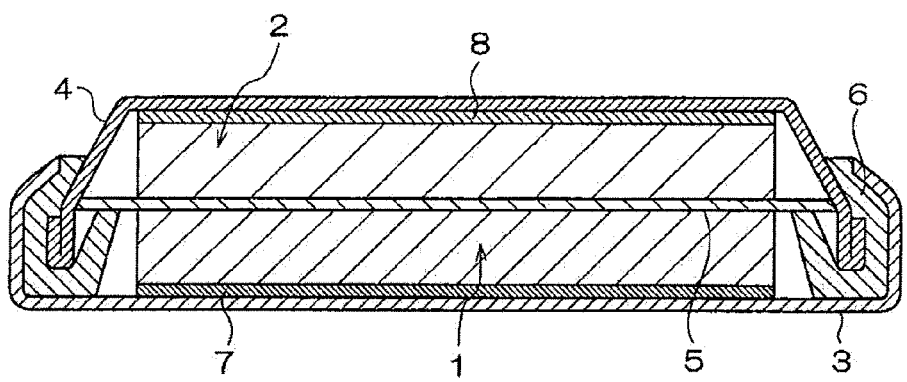

NON-AQUEOUS ELECTROLYTE SOLUTION FOR BATTERY AND LITHIUM SECONDARY BATTERY

TECHNICAL FIELD

The present invention relates to a non-aqueous electrolyte solution for a battery and a lithium secondary battery that can be charged and discharged and that be used, for example, for a power source of a portable electric instrument, for adapting for car, or for electric power storage.

BACKGROUND ART

In recent years, lithium secondary batteries are widely used as power sources for electronic devices such as portable telephones and notebook computers, or for electric cars or electric power storage. Particularly recently, there is a rapidly increasing demand for a high capacity and high power battery with a high energy density, which can be mounted in hybrid cars or electric cars.

Lithium secondary batteries are primarily composed of a positive electrode and a negative electrode, which contain materials capable of absorption and desorption of lithium, and a non-aqueous electrolyte solution containing a lithium salt and a non-aqueous solvent.

Examples of positive electrode active materials used in a positive electrode include lithium metal oxides such as $LiCoO_2$, $LiMnO_2$, $LiNiO_2$, and $LiFePO_4$.

Furthermore, as the non-aqueous electrolyte solution, solutions prepared by mixing a mixed solvent (non-aqueous solvent) of carbonates such as ethylene carbonate, propylene carbonate, ethylene carbonate or methyl carbonate, with a Li electrolyte such as $LiPF_6$, $LiBF_4$, $LiN(SO_2CF_3)_2$ or $LiN(SO_2CF_2CF_3)_2$, are used.

On the other hand, as the active material for a negative electrode which is used in negative electrodes, metal lithium, metal compounds (elemental metals, oxides, alloys with lithium, and the like) capable of absorption and desorption of lithium, and carbon materials are known. Particularly, lithium secondary batteries employing cokes, artificial graphite or natural graphite, which are all capable of absorption and desorption of lithium, have been put to practical use.

As an attempt to improve battery performance, it is proposed to incorporate various additives into a non-aqueous electrolyte solution. For example, a non-aqueous electrolyte solution including a cyclic sulfate ester as an additive is known (for example, see WO 2012/053644).

SUMMARY OF INVENTION

Technical Problem

However, there is a desire for further improvement in battery resistance characteristics (i.e., further reduction in initial (pre-storage) and post-storage battery resistance).

The present invention has been accomplished to solve the above problem. It is an object of the invention to provide a non-aqueous electrolyte solution for a battery that can significantly improve battery resistance characteristics and a lithium secondary battery whose resistance characteristics have been significantly improved.

Solution to Problem

The inventors of the invention conducted a thorough investigation to solve the above problem and consequently found that adding a specific compound to a non-aqueous electrolyte solution for a battery can significantly improve battery resistance characteristics, thus completing the invention.

Specifically, means for solving the problem are as follows:

<1> A non-aqueous electrolyte solution for a battery, comprising:
an additive A which is a cyclic sulfate compound represented by the following formula (I); and
an additive B which is at least one selected from the group consisting of an aromatic compound having at least one of a halogen atom or an alkyl group and a carbamate compound, and which is a compound other than a carbonate compound and a cyclic sulfate compound:

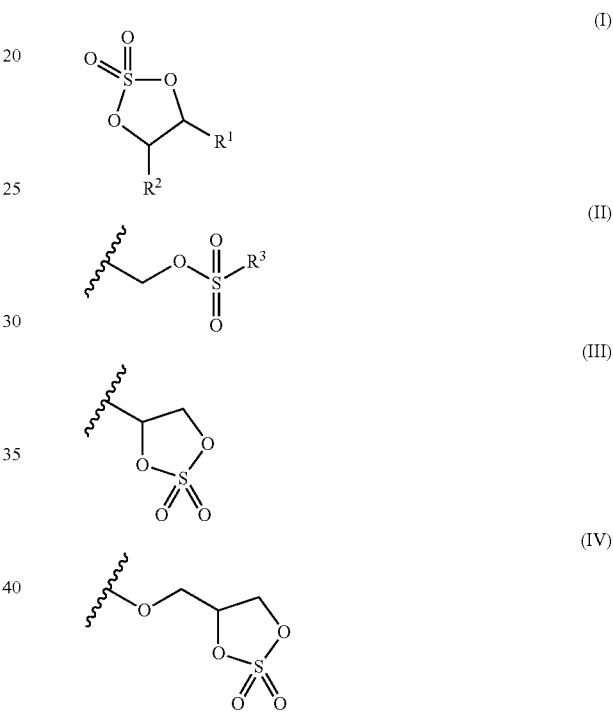

wherein, in formula (I), $R^1$ represents a group represented by formula (II) or a group represented by formula (III) and $R^2$ represents a hydrogen atom, an alkyl group having from 1 to 6 carbon atoms, a group represented by formula (II) or a group represented by formula (III), or $R^1$ and $R^2$ represent groups which combine to form a benzene ring or a cyclohexyl ring together with a carbon atom to which $R^1$ is bonded and a carbon atom to which $R^2$ is bonded;

in formula (II), $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by formula (IV), and wavy lines in formula (II), formula (III), and formula (IV) represent bonding positions; and in a case in which there are two groups represented by formula (II) in the cyclic sulfate compound represented by formula (I), the two groups represented by formula (II) may be the same as or different from each other.

<2> The non-aqueous electrolyte solution for a battery according to <1>, wherein in formula (I), $R^1$ represents a group represented by formula (II) (provided that in formula (II), $R^3$ represents a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III); and $R^2$ represents a hydrogen atom, an alkyl group having from 1 to 3 carbon atoms, a group represented by formula (II) (provided that in formula (II), $R^3$ represents a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III).

<3> The non-aqueous electrolyte solution for a battery according to <1>, wherein in formula (I), $R^1$ represents a group represented by formula (II) (provided that in formula (II), $R^3$ represents a fluorine atom, a methyl group, an ethyl group, a trifluoromethyl group, a methoxy group, an ethoxy group, or a group represented by formula (IV)) or a group represented by formula (III); and $R^2$ represents a hydrogen atom or a methyl group.

<4> The non-aqueous electrolyte solution for a battery according to any one of <1> to <3>, wherein the additive B is at least one selected from the group consisting of: an aromatic hydrocarbon compound substituted with at least one selected from the group consisting of a fluorine atom, a chlorine atom and an alkyl group having from 1 to 6 carbon atoms; and a cyclic carbamate compound represented by the following formula (V):

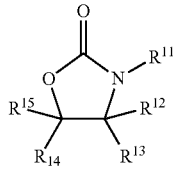

(V)

wherein in formula (V), $R^{11}$ represents a hydrogen atom or an alkyl group having from 1 to 6 carbon atoms, and $R^{12}$ to $R^{15}$ each independently represent a hydrogen atom, a halogen atom, or an alkyl group having from 1 to 6 carbon atoms.

<5> The non-aqueous electrolyte solution for a battery according to <4>, wherein in formula (V), $R^{11}$ to $R^{15}$ each independently represent a hydrogen atom or an alkyl group having from 1 to 3 carbon atoms.

<6> The non-aqueous electrolyte solution for a battery according to any one of <1> to <5>, further comprising an additive C which is at least one selected from the group consisting of a carbonate compound having a carbon-carbon unsaturated bond, a carbonate compound having a fluorine atom, a fluorophosphate compound, an oxalato compound, a cyclic sultone compound, and an alicyclic compound having a fluorine atom.

<7> The non-aqueous electrolyte solution for a battery according to <6>, wherein the additive C is at least one selected from the group consisting of vinylene carbonate, vinylethylene carbonate, 4-fluoroethylene carbonate, 4,4-difluoroethylene carbonate, 4,5-difluoroethylene carbonate, lithium monofluorophosphate, lithium difluorophosphate, lithium difluorobis(oxalato)phosphate, lithium bisoxalato borate, 1,3-propane sultone, 1,3-propene sultone, and 1,1,2,2,3,3,4-heptafluorocyclopentane.

<8> The non-aqueous electrolyte solution for a battery according to any one of <1> to <7>, wherein a content of the additive A is from 0.001 mass % to 10 mass % with respect to the total amount of the non-aqueous electrolyte solution for a battery.

<9> The non-aqueous electrolyte solution for a battery according to any one of <1> to <7>, wherein a content of the additive B is from 0.001 mass % to 20 mass % with respect to the total amount of the non-aqueous electrolyte solution for a battery.

<10> The non-aqueous electrolyte solution for a battery according to any one of <1> to <8>, wherein a content of the additive A is from 0.001 mass % to 10 mass % with respect to the total amount of the non-aqueous electrolyte solution for a battery, and a content of the additive B is from 0.001 mass % to 20 mass % with respect to the total amount of the non-aqueous electrolyte solution for a battery.

<11> The non-aqueous electrolyte solution for a battery according to any one of <1> to <10>, wherein a content mass ratio of the additive B to the additive A (additive B/additive A) is from 1.0 to 20.0.

<12> The non-aqueous electrolyte solution for a battery according to <6> or <7>, wherein a content of the additive C is from 0.001 mass % to 10 mass % with respect to a total amount of the non-aqueous electrolyte solution for a battery.

<13> A lithium secondary battery comprising a positive electrode; a negative electrode including, as a negative electrode active material, at least one selected from the group consisting of metal lithium, a lithium-containing alloy, a metal or alloy capable of alloying with lithium, an oxide capable of doping and dedoping lithium ions, a transition metal nitride capable of doping and dedoping lithium ions, and a carbon material capable of doping and dedoping lithium ions; and the non-aqueous electrolyte solution for a battery according to any one of <1> to <12>.

<14> A lithium secondary battery obtained by charging and discharging a lithium secondary battery comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping lithium ions, a transition metal nitride capable of doping and dedoping lithium ions, and a carbon material capable of doping and dedoping lithium ions; and the non-aqueous electrolyte solution for a battery according to any one of <1> to <12>.

Advantageous Effects of Invention

According to the invention, a non-aqueous electrolyte solution for a battery that can significantly improve battery resistance characteristics and a lithium secondary battery whose resistance characteristics have been significantly improved can be provided.

BRIEF DESCRIPTION OF DRAWING

FIG. 1 is a schematic cross-sectional diagram of a coin battery illustrating an example of a lithium secondary battery of the invention.

DESCRIPTION OF EMBODIMENTS

Hereinafter, a detailed description will be given of a non-aqueous electrolyte solution for a battery of the invention and a lithium secondary battery thereof.

[Non-Aqueous Electrolyte Solution for Battery]

The non-aqueous electrolyte solution for a battery of the invention (hereinafter also referred to simply as "non-aqueous electrolyte solution") includes an additive A which is a cyclic sulfate compound represented by formula (I) to be described later and an additive B which is at least one selected from the group consisting of an aromatic compound having at least one of a halogen atom or an alkyl group and a carbamate compound and which is a compound other than a carbonate compound and a cyclic sulfate compound.

With the above structure, the non-aqueous electrolyte solution of the invention can significantly improve battery resistance characteristics. Specifically, the non-aqueous electrolyte solution of the invention can significantly reduce initial battery resistance and post-storage battery resistance.

Reasons that such an effect can be obtained are assumed to be as follows:

One of factors that increase battery resistance is considered to be decomposition of a solvent on a negative electrode surface. Specifically, it is considered that since lithium metal is present in a negative electrode active material on the negative electrode surface under charging conditions, a reductive decomposition reaction of the solvent occurs. When such a reductive decomposition reaction continuously occurs, battery resistance will increase.

In terms of the increase in battery resistance described above, the use of the non-aqueous electrolyte solution of the invention is considered to cause a component derived from the additive A (a cyclic sulfate compound) to form a passivation film on the negative electrode surface first at the time of initial charging. The passivation film is considered to suppress contact between the negative electrode surface and the solvent and the decomposition of the solvent on the negative electrode surface, resulting in suppression of increase in battery resistance.

In addition, it has turned out that the use of the non-aqueous electrolyte solution of the invention more effectively suppresses increase in battery resistance than the use of a non-aqueous electrolyte solution that includes the additive A but does not include the additive B.

Although the reason for this is not clear, it is conceivable that the use of the non-aqueous electrolyte solution of the invention including both the additive A and the additive B allows a reaction or interaction between the additive A-derived passivation film component first formed on the negative electrode surface and the additive B, thereby forming a passivation film having a more favorable quality.

The reason that the reaction or interaction between the additive A-derived passivation film component and the additive B is possible is presumed to be because the additive B, which is at least one selected from the group consisting of an aromatic compound having at least one of a halogen atom or an alkyl group and a carbamate compound, has at least one of a carbon-carbon unsaturated bond or a carbon-oxygen unsaturated bond.

Meanwhile, it is known that an aromatic compound having at least one of a halogen atom or an alkyl group and a carbamate compound, which serve as the additive B, are used particularly in high-capacity batteries and high-voltage batteries, and are also used in providing an overcharging prevention function (for example, see Japanese Patent No. 4212301, No. 4205863, No. 3113652, No. 4492023, and No. 4259789).

However, investigation by the present inventors has shown that there are cases in which these compounds instead degrade an original performance of a battery (for example, a performance such as initial or post-storage battery resistance) under normal battery operating conditions (for example, conditions such as a charging voltage of 4.6 V or less, and particularly conditions such as a charging voltage of 4.2 V or less).

In connection with the above problem, it has been shown that the non-aqueous electrolyte solution of the invention including not only the additive B but also the additive A can suppress increase in battery resistance without degrading the performance of a battery under such normal battery operating conditions. The reason for this is not clear, but it can be speculated that the passivation film made of the additive A-derived component and formed on the negative electrode surface suppresses contact between the negative electrode surface and the additive B and decomposition of the additive B on the negative electrode surface.

The non-aqueous electrolyte solution of the invention can significantly reduce post-storage battery resistance and is therefore expected to have an effect of extending a service life of battery (i.e., an effect of improving battery storage performance).

Additionally, the non-aqueous electrolyte solution of the invention includes the additive B and is therefore expected to be provided with an overcharging prevention function.

Hereinafter, the components of the non-aqueous electrolyte solution of the invention will be specifically described.

<Additive A (Cyclic Sulfate Compound)>

The non-aqueous electrolyte solution of the invention includes the additive A which is a cyclic sulfate compound represented by the following formula (I).

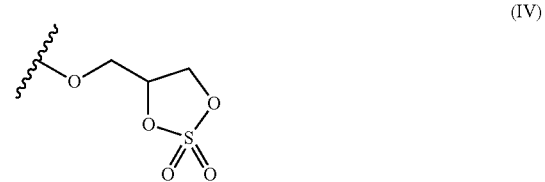

In formula (I), $R^1$ represents a group represented by formula (II) or a group represented by formula (III) and $R^2$ represents a hydrogen atom, an alkyl group having from 1 to 6 carbon atoms, a group represented by formula (II) or a group represented by formula (III), or $R^1$ and $R^2$ represent groups which combine to form a benzene ring or a cyclohexyl ring together with a carbon atom to which $R^1$ is bonded and a carbon atom to which $R^2$ is bonded;

in formula (II), $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by formula (IV), and wavy lines in formula (II), formula (III), and formula (IV) represent bonding positions; and in a case in which there are two groups represented by formula (II) in the cyclic sulfate compound represented by formula (I), the two groups represented by formula (II) may be the same as or different from each other.

In formula (II), specific examples of "the halogen atom" include a fluorine atom, a chlorine atom, a bromine atom, and an iodine atom.

The halogen atom is preferably a fluorine atom.

In formula s (I) and (II), "the alkyl group having from 1 to 6 carbon atoms" is a linear or branched chain alkyl group having from 1 to 6 carbon atoms, and specific examples thereof include a methyl group, an ethyl group, a propyl group, an isopropyl group, a butyl group, an isobutyl group, a sec-butyl group, a tert-butyl group, a pentyl group, a 2-methylbutyl group, a 1-methylpentyl group, a neopentyl group, a 1-ethylpropyl group, a hexyl group, and a 3,3-dimethylbutyl group.

The alkyl group having from 1 to 6 carbon atoms is more preferably an alkyl group having from 1 to 3 carbon atoms.

In formula (II), "the halogenated alkyl group having from 1 to 6 carbon atoms" is a linear or branched chain halogenated alkyl group having from 1 to 6 carbon atoms, and specific examples thereof include a fluoromethyl group, a difluoromethyl group, a trifluoromethyl group, a 2,2,2-trifluoroethyl group, a perfluoroethyl group, a perfluoropropyl group, a perfluorobutyl group, a perfluoropentyl group, a perfluorohexyl group, a perfluoroisopropyl group, a perfluoroisobutyl group, a chloromethyl group, a chloroethyl group, a chloropropyl group, a bromomethyl group, a bromoethyl group, a bromopropyl group, an iodomethyl group, an iodoethyl group, and an iodopropyl group.

The halogenated alkyl group having from 1 to 6 carbon atoms is more preferably a halogenated alkyl group having from 1 to 3 carbon atoms.

In formula (II), the "alkoxy group having from 1 to 6 carbon atoms" is a linear or branched chain alkoxy group having from 1 to 6 carbon atoms, and specific examples thereof include a methoxy group, an ethoxy group, a propoxy group, an isopropoxy group, a butoxy group, an isobutoxy group, a sec-butoxy group, a tert-butoxy group, a pentyloxy group, a 2-methyl-butoxy group, a 1-methylpentyloxy group, a neopentyloxy group, a 1-ethylpropoxy group, a hexyloxy group, and a 3,3-dimethyl-butoxy group.

The alkoxy group having from 1 to 6 carbon atoms is more preferably an alkoxy group having from 1 to 3 carbon atoms.

A preferable embodiment of formula (I) is an embodiment in which $R^1$ is a group represented by formula (II) (in formula (II), $R^3$ is preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III), and $R^2$ is a hydrogen atom, an alkyl group having from 1 to 3 carbon atoms, a group represented by formula (II), or a group represented by formula (III), or $R^1$ and $R^2$ are groups which combine to form a benzene ring or a cyclohexane ring together with a carbon atom to which $R^1$ is bonded and a carbon atom to which $R^2$ is bonded.

$R^1$ in formula (I) is more preferably a group represented by formula (II) (in formula (II), $R^3$ is particularly preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III).

$R^2$ in formula (I) is more preferably a hydrogen atom, an alkyl group having from 1 to 3 carbon atoms, a group represented by formula (II) (in formula (II), $R^3$ is still more preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III), still more preferably a hydrogen atom or a methyl group, and particularly preferably a hydrogen atom.

In a case in which $R^1$ in formula (I) is a group represented by formula (II), $R^3$ in formula (II) is a halogen atom, an alkyl group having from 1 to 6 carbon atoms, a halogenated alkyl group having from 1 to 6 carbon atoms, an alkoxy group having from 1 to 6 carbon atoms, or a group represented by formula (IV), as described above. However, $R^3$ is more preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV), and still more preferably a fluorine atom, a methyl group, an ethyl group, a trifluoromethyl group, a methoxy group, an ethoxy group, or a group represented by formula (IV).

In a case in which $R^2$ in formula (I) is a group represented by formula (II), $R^3$ in formula (II) has the same preferable definition as $R^3$ in the case where $R^1$ in formula (I) is a group represented by formula (II).

A preferable combination of $R^1$ and $R^2$ in formula (I) is a combination in which $R^1$ is a group represented by formula (II) (in formula (II), $R^3$ is preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III), and $R^2$ is a hydrogen atom, an alkyl group having from 1 to 3 carbon atoms, a group represented by formula (II) (in formula (II), $R^3$ is preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III).

A more preferable combination of $R^1$ and $R^2$ in formula (I) is a combination in which $R^1$ is a group represented by formula (II) (in formula (II), $R^3$ is preferably a fluorine atom, a methyl group, an ethyl group, a trifluoromethyl group, a methoxy group, an ethoxy group, or a group represented by formula (IV)), or a group represented by formula (III), and $R^2$ is a hydrogen atom or a methyl group.

A particularly preferable combination of $R^1$ and $R^2$ in formula (I) is a combination in which in formula (I), $R^1$ is a group represented by formula (III) and $R^2$ is a hydrogen atom (most preferably 1,2:3,4-di-O-sulfanyl-meso-erythritol).

Examples of the cyclic sulfate compound represented by formula (I) include catechol sulfate, 1,2-cyclohexyl sulfate, and compounds represented by the following exemplary compounds 1 to 30, provided that the cyclic sulfate compound represented by formula (I) is not limited thereto.

In the structures of the following exemplary compounds, "Me" represents a methyl group, "Et" represents an ethyl group, "Pr" represents a propyl group, "iPr" represents an isopropyl group, "Bu" represents a butyl group, "tBu"

represents a tertiary butyl group, "Pent" represents a pentyl group, "Hex" represents a hexyl group, "OMe" represents a methoxy group, "OEt" represents an ethoxy group, "OPr" represents a propoxy group, "OBu" represents a butoxy group, "OPent" represents a pentyloxy group, and "OHex" represents a hexyloxy group, respectively. Furthermore, "wavy lines" in $R^1$ to $R^3$ represent bonding positions.

Stereoisomers derived from the substituents at the 4-position and 5-position of a 2,2-dioxo-1,3,2-dioxathiolane ring may occur, and both are compounds that are included in the invention.

In cases in which the cyclic sulfate compound represented by formula (I) has two or more asymmetric carbon atoms in the molecule thereof, each compound has stereoisomers (diastereomers). In such cases, each compound means a mixture of corresponding diastereomers unless particularly stated otherwise.

| Exemplary Compound No. | $R^1$ | $R^2$ | $R^3$ |
|---|---|---|---|
| 1 | —CH₂CH₂—O—S(=O)₂—$R^3$ | H | Me |
| 2 | —CH₂CH₂—O—S(=O)₂—$R^3$ | H | Et |
| 3 | —CH₂CH₂—O—S(=O)₂—$R^3$ | H | Pr |
| 4 | —CH₂CH₂—O—S(=O)₂—$R^3$ | H | iPr |
| 5 | —CH₂CH₂—O—S(=O)₂—$R^3$ | H | Bu |
| 6 | —CH₂CH₂—O—S(=O)₂—$R^3$ | H | tBu |
| 7 | —CH₂CH₂—O—S(=O)₂—$R^3$ | H | Pent |
| 8 | —CH₂CH₂—O—S(=O)₂—$R^3$ | H | Hex |

-continued
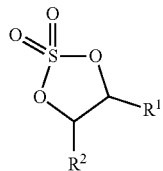
(I)
| Exemplary Compound No. | R¹ | R² | R³ |
|---|---|---|---|
| 9 | ~O-S(=O)₂-R³ | H | $CF_3$ |
| 10 | ~O-S(=O)₂-R³ | H | $CHF_2$ |
| 11 | ~O-S(=O)₂-R³ | H | $CH_2CF_3$ |
| 12 | ~O-S(=O)₂-R³ | H | $CH_2CH_2CF_3$ |
| 13 | ~O-S(=O)₂-R³ | H | $CH_2CH_2CH_2CF_3$ |
| 14 | ~O-S(=O)₂-R³ | H | $CH_2CH_2CH_2CH_2CF_3$ |
| 15 | ~O-S(=O)₂-R³ | H | $CH_2CH_2CH_2CH_2CH_2CF_3$ |
| 16 | ~O-S(=O)₂-R³ | H | ~O-CH₂-(cyclic sulfate) |
| 17 | ~O-S(=O)₂-R³ | Me | Me |
| 18 | ~O-S(=O)₂-R³ | Et | Me |

-continued
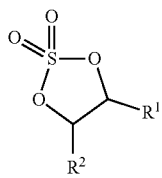
(I)
| Exemplary Compound No. | R¹ | R² | R³ |
|---|---|---|---|
| 19 | -CH₂CH₂-O-S(=O)₂-R³ | Hex | Me |
| 20 | -CH₂CH₂-O-S(=O)₂-R³ | -CH₂CH₂-O-S(=O)₂-R³ | Me |
| 21 | -CH₂CH₂-O-S(=O)₂-R³ | -CH₂CH₂-O-S(=O)₂-R³ | Et |
| 22 | cyclic sulfate (1,3,2-dioxathiolane 2,2-dioxide) | H | — |
| 23 | cyclic sulfate (1,3,2-dioxathiolane 2,2-dioxide) | cyclic sulfate (1,3,2-dioxathiolane 2,2-dioxide) | — |
| 24 | -CH₂CH₂-O-S(=O)₂-R³ | H | F |
| 25 | -CH₂CH₂-O-S(=O)₂-R³ | H | OMe |
| 26 | -CH₂CH₂-O-S(=O)₂-R³ | H | OEt |
| 27 | -CH₂CH₂-O-S(=O)₂-R³ | H | OPr |

-continued

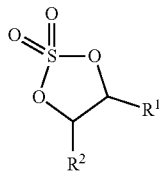
(I)

| Exemplary Compound No. | $R^1$ | $R^2$ | $R^3$ |
|---|---|---|---|
| 28 | ～O-S(=O)(=O)-$R^3$ (via CH2CH2O) | H | OBu |
| 29 | ～O-S(=O)(=O)-$R^3$ (via CH2CH2O) | H | OPent |
| 30 | ～O-S(=O)(=O)-$R^3$ (via CH2CH2O) | H | OHex |

The cyclic sulfate compound represented by formula (I) is preferably catechol sulfate, an exemplary compound 1, an exemplary compound 2, an exemplary compound 16, an exemplary compound 22, an exemplary compound 23, and exemplary compounds 24 to 28, and particularly preferably catechol sulfate, the exemplary compound 1, the exemplary compound 2, the exemplary compound 16, and the exemplary compound 22.

The non-aqueous electrolyte solution of the invention may include only one kind of additive A (i.e., a cyclic sulfate compound represented by formula (I)) or may include two or more kinds of additives A.

A content (if two or more kinds are included, a total content; and the same shall apply hereinafter) of the additive A in the non-aqueous electrolyte solution of the invention is not particularly limited. The content of the additive A is preferably from 0.001 mass % to 10 mass %, more preferably from 0.05 mass % to 5 mass %, still more preferably from 0.1 mass % to 4 mass %, still more preferably from 0.1 mass % to 2 mass %, and particularly preferably from 0.5 mass % to 2 mass %, from the viewpoint of more effectively exhibiting the effect of the invention.

In the present specification, the term "content of the additive" and the term "addition amount of the additive" both mean a content of the additive with respect to the total amount of the non-aqueous electrolyte solution.

<Additive B>

The non-aqueous electrolyte solution of the invention includes the additive B.

The additive B is at least one selected from the group consisting of an aromatic compound having at least one of a halogen atom or an alkyl group and a carbamate compound, and the additive B is a compound other than a carbonate compound and a cyclic sulfate compound (i.e., a compound which is neither a carbonate compound nor a cyclic sulfate compound).

The aromatic compound having at least one of a halogen atom or an alkyl group is a compound having a carbon-carbon unsaturated bond, and the carbamate compound is a compound having a carbon-oxygen unsaturated bond.

(Aromatic Compound Having at Least One of Halogen Atom or Alkyl Group)

Examples of the halogen atom in the aromatic compound having at least one of a halogen atom or an alkyl group include a fluorine atom, a chlorine atom, a bromine atom, and an iodine atom, in which a fluorine atom and a chlorine atom are preferable, and a fluorine atom is more preferable.

Examples of the alkyl group in the aromatic compound having at least one of a halogen atom or an alkyl group include an alkyl group having from 1 to 10 carbon atoms, in which an alkyl group having from 1 to 6 carbon atoms is preferable.

The aromatic compound having at least one of a halogen atom or an alkyl group is preferably an aromatic compound substituted with at least one substituent selected from the group consisting of a halogen atom, an alkyl group, and a halogenated alkyl group (i.e., a substituted aromatic compound formed by substituting an unsubstituted aromatic compound with at least one substituent selected from the group consisting of a halogen atom, an alkyl group, and a halogenated alkyl group).

Examples of the halogenated alkyl group include an alkyl group having from 1 to 10 (preferably, from 1 to 6) carbon atoms substituted with at least one halogen atom.

Examples of the unsubstituted aromatic compound include aromatic hydrocarbon compounds such as benzene, naphthalene, anthracene, biphenyl, and terphenyl; and heteroaromatic compounds such as pyridine.

The unsubstituted aromatic compound have preferably from 1 to 12 carbon atoms.

The unsubstituted aromatic compound are preferably an unsubstituted aromatic compound having from 1 to 12 carbon atoms, more preferably an unsubstituted aromatic hydrocarbon compound having from 1 to 12 carbon atoms, and particularly preferably benzene or biphenyl.

The aromatic compound having at least one of a halogen atom or an alkyl group is particularly preferably an aromatic hydrocarbon compound substituted with at least one selected from the group consisting of a fluorine atom, a chlorine atom, and an alkyl group having from 1 to 6 carbon atoms.

Examples of the aromatic compound having at least one of a halogen atom or an alkyl group include halogenated benzenes such as fluorobenzene, chlorobenzene, 1,2-difluorobenzene, 1,2-dichlorobenzene, 1,3-difluorobenzene, 1,3-dichlorobenzene, 1,4-difluorobenzene, 1,4-dichlorobenzene, 1,2,3-trifluorobenzene, 1,2,4-trifluorobenzene, 1,3,5-trifluorobenzene, 1,2,4,5-tetrafluorobenzene, pentafluorobenzene, and hexafluorobenzene; halogenated toluenes such as 2-fluorotoluene, 2-chlorotoluene, 3-fluorotoluene, 3-chlorotoluene, 4-fluorotoluene, 4-chlorotoluene, 2,3-difluorotoluene, 2,4-difluorotoluene, 2,5-difluorotoluene, 2,6-difluorotoluene, α-fluorotoluene, α,α-difluorotoluene, and α,α,α-trifluorotoluene; halogenated biphenyls such as 2-fluorobiphenyl, 2-chlorobiphenyl, 3-fluorobiphenyl, 3-chlorobiphenyl, 4-fluorobiphenyl, 4-chlorobiphenyl, 2,2'-difluorobiphenyl, 3,3'-difluorobiphenyl, and 4,4'-difluorobiphenyl; chain alkylbenzenes such as toluene, xylene, ethylbenzene, propylbenzene, isopropylbenzene, butylbenzene, sec-butylbenzene, tert-butylbenzene, pentylbenzene, tert-amylbenzene, and hexylbenzene; and cyclic alkylbenzenes such as cyclopentylbenzene and cyclohexylbenzene.

Among them, fluorobenzene, chlorobenzene, 2-fluorotoluene, 2-chlorotoluene, 3-fluorotoluene, 3-chlorotoluene, 2-fluorobiphenyl, and cyclohexylbenzene are preferable; and fluorobenzene, 2-fluorotoluene, 2-fluorobiphenyl, and cyclohexylbenzene are particularly preferable.

(Carbamate Compound)

Examples of the carbamate compound include a cyclic carbamate compound represented by the following formula (V) and a chain carbamate compound represented by the following formula (VI).

Among the compounds, the cyclic carbamate compound represented by formula (V) is more preferable.

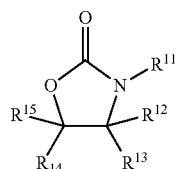

(V)

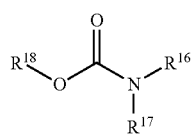

(VI)

In formula (V), $R^{11}$ represents a hydrogen atom or an alkyl group having from 1 to 10 carbon atoms that may be substituted, and $R^{12}$ to $R^{15}$ each independently represent a hydrogen atom, a halogen atom, or an alkyl group that has from 1 to 10 carbon atoms and that may be substituted.

In formula (VI), $R^{16}$ and $R^{17}$ each independently represent a hydrogen atom or an alkyl group that has from 1 to 10 carbon atoms and that may be substituted, and $R^{18}$ represents a hydrogen atom, a halogen atom, or an alkyl group that has from 1 to 10 carbon atoms and that may be substituted.

In formulae (V) and (VI), examples of a substituent in "an alkyl group that has from 1 to 10 carbon atoms and that may be substituted" include a halogen atom, an alkoxy group (preferably an alkoxy group having from 1 to 10 carbon atoms, more preferably an alkoxy group having from 1 to 6 carbon atoms, and still more preferably an alkoxy group having from 1 to 3 carbon atoms), a phenyl group, a phenoxy group, and amino group.

In addition, examples of "the alkyl group that has from 1 to 10 carbon atoms" in "the alkyl group that has from 1 to 10 carbon atoms and that may be substituted" include linear chain, branched chain and cyclic alkyl groups that have from 1 to 10 carbon atoms, and specific examples thereof include a methyl group, an ethyl group, a propyl group, an isopropyl group, a butyl group, an isobutyl group, a sec-butyl group, a tert-butyl group, a pentyl group, a 2-methylbutyl group, a 1-methylpentyl group, a neopentyl group, a 1-ethylpropyl group, a hexyl group, a cyclohexyl group, a 3,3-dimethylbutyl group, a heptyl group, an octyl group, a nonyl group, and a decyl group.

The alkyl group having from 1 to 10 carbon atoms is preferably an alkyl group having from 1 to 6 carbon atoms.

In formula (V), $R^{11}$ is preferably a hydrogen atom or an alkyl group having from 1 to 6 carbon atoms (i.e., an unsubstituted alkyl group having from 1 to 6 carbon atoms, and the same shall apply hereinafter), and more preferably a halogen atom or an alkyl group having from 1 to 3 carbon atoms (i.e., an unsubstituted alkyl group having from 1 to 3 carbon atoms, and the same shall apply hereinafter).

In formula (V), $R^{12}$ to $R^{15}$ are preferably each independently a hydrogen atom, a halogen atom, or an alkyl group having from 1 to 6 carbon atoms, more preferably each independently a hydrogen atom, a halogen atom, or an alkyl group having from 1 to 3 carbon atoms, and particularly preferably each independently a hydrogen atom or an alkyl group having from 1 to 3 carbon atoms.

In formula (V), $R^{11}$ to $R^{15}$ are particularly preferably each independently a hydrogen atom or an alkyl group having from 1 to 3 carbon atoms.

In addition, in formula (VI), $R^{16}$ and $R^{17}$ are preferably each independently a hydrogen atom or an alkyl group having from 1 to 6 carbon atoms, and more preferably each independently a hydrogen atom or an alkyl group having from 1 to 3 carbon atoms.

The cyclic carbamate compound represented by formula (V) is particularly preferably N-methyl oxazolidinone or N-ethyl oxazolidinone.

The chain carbamate compound represented by formula (VI) is particularly preferably N,N-dimethyl cyclohexyl carbamate or N,N-diethyl cyclohexyl carbamate.

The additive B described above is particularly preferably at least one selected from the group consisting of an aromatic hydrocarbon compound substituted with at least one selected from the group consisting of a fluorine atom, a chlorine atom, and an alkyl group having from 1 to 6 carbon atoms and the cyclic carbamate compound represented by formula (V), from the viewpoint of more effectively exhibiting the effect of the invention.

Preferable embodiments of the aromatic hydrocarbon compound and the cyclic carbamate compound represented by formula (V) are as respectively described above.

Among them, the additive B is preferably at least one selected from the group consisting of fluorobenzene, chlorobenzene, 2-fluorotoluene, 2-chlorotoluene, 3-fluorotoluene, 3-chlorotoluene, 2-fluorobiphenyl, cyclohexyl benzene, N-methyl oxazolidinone, and N-ethyl oxazolidinone, more preferably at least one selected from the group consisting of fluorobenzene, 2-fluorotoluene, 2-fluorobiphenyl, cyclohexylbenzene, N-methyl oxazolidinone, and N-ethyl oxazolidinone, and particularly preferably at least one selected from the group consisting of fluorobenzene, 2-fluorotoluene, 2-fluorobiphenyl, and cyclohexylbenzene.

The non-aqueous electrolyte solution of the invention may include only one kind of additive B or may include two or more kinds of additives B.

A content of the additive B in the non-aqueous electrolyte solution of the invention (if two or more kinds are included, a total content; and the same shall apply hereinafter) is not particularly limited. The content of the additive B is preferably from 0.001 mass % to 20 mass %, more preferably from 0.001 mass % to 15 mass %, more preferably from 0.001 mass % to 10 mass %, still more preferably from 0.1 mass % to 8 mass %, and particularly preferably from 0.5 mass % to 8 mass %, from the viewpoint of more effectively providing the advantageous effect of the invention. Alternatively, the content of the additive B is particularly preferably from 2 mass % to 10 mass %.

In addition, particularly preferably, the content of the additive A is from 0.001 mass % to 10 mass % and the content of the additive B is from 0.001 mass % to 20 mass % (still more preferably from 0.001 mass % to 10 mass %), from the viewpoint of more effectively exhibiting the effect of the invention (the effect obtained by the combination of the additive A and the additive B).

Additionally, a content mass ratio of the additive B to the additive A (additive B/additive A) is preferably from 1.0 to 20.0, more preferably from more than 1.0 to 20.0, still more preferably from 2.0 to 20.0, still more preferably from 4.0 to 20.0, and particularly preferably from 4.0 to 10.0, from the viewpoint of more effectively exhibiting the effect of the invention (the effect obtained by the combination of the additive A and the additive B).

When the content mass ratio (additive B/additive A) is from 1.0 to 20.0, the effect of the combination of the additive A and the additive B is more effectively exhibited.

In the non-aqueous electrolyte solution of the invention, preferable combinations of the additive A and the additive B are those obtained by optionally combining the preferable embodiments of the additive A described above and the preferable embodiments of the additive B described above.

Among the combinations thereof, from the viewpoint of particularly significantly exhibiting the effect of the invention, preferable combinations of the additive A and the additive B are as follows:

A preferable combination of, as the additive A, a cyclic sulfate compound in which, in formula (I), $R^1$ is a group represented by formula (II) (provided that, in formula (II), $R^3$ represents a fluorine atom, a methyl group, an ethyl group, a trifluoromethyl group, a methoxy group, an ethoxy group, or a group represented by formula (IV)) or a group represented by formula (III), and $R^2$ represents a hydrogen atom or a methyl group, and as the additive B, at least one selected from the group consisting of an aromatic hydrocarbon compound substituted with at least one selected from the group consisting of a fluorine atom, a chlorine atom, and an alkyl group having from 1 to 6 carbon atoms and a cyclic carbamate compound represented by formula (V) (provided that, in formula (V), $R^{11}$ to $R^{15}$ each independently represent a hydrogen atom or an alkyl group having from 1 to 3 carbon atoms);

a more preferable combination of, as the additive A, a cyclic sulfate compound in which, in formula (I), $R^1$ is a group represented by formula (II) (provided that, in formula (II), $R^3$ represents a fluorine atom, a methyl group, an ethyl group, a trifluoromethyl group, a methoxy group, an ethoxy group, or a group represented by formula (IV)) or a group represented by formula (III), and $R^2$ represents a hydrogen atom or a methyl group, and as the additive B, at least one selected from the group consisting of fluorobenzene, chlorobenzene, 2-fluorotoluene, 2-chlorotoluene, 3-fluorotoluene, 3-chlorotoluene, 2-fluorobiphenyl, cyclohexylbenzene, N-methyl oxazolidinone, and N-ethyl oxazolidinone; and a particularly preferable combination of, as the additive A, a cyclic sulfate compound in which, in formula (I) $R^1$ is a group represented by formula (II) (provided that, in formula (II), $R^3$ represents a fluorine atom, a methyl group, an ethyl group, a trifluoromethyl group, a methoxy group, an ethoxy group, or a group represented by formula (IV)) or a group represented by formula (III), and $R^2$ is a hydrogen atom or a methyl group, and as the additive B, at least one selected from the group consisting of fluorobenzene, 2-fluorotoluene, 2-fluorobiphenyl, and cyclohexylbenzene.

<Additive C>

The non-aqueous electrolyte solution of the invention preferably further includes an additive C which is at least one selected from the group consisting of a carbonate compound having a carbon-carbon unsaturated bond, a carbonate compound substituted with a fluorine atom, a fluorophosphate compound, an oxalato compound, a cyclic sultone compound, and an alicyclic compound having a fluorine atom.

(Carbonate Compound Having Carbon-Carbon Unsaturated Bond)

Examples of the carbonate compound having a carbon-carbon unsaturated bond include chain carbonates such as methylvinyl carbonate, ethylvinyl carbonate, divinyl carbonate, methyl propynyl carbonate, ethyl propynyl carbonate, dipropynyl carbonate, methylphenyl carbonate, ethylphenyl carbonate, and diphenyl carbonate; and cyclic carbonates such as vinylene carbonate, methylvinylene carbonate, 4,4-dimethylvinylene carbonate, 4,5-dimethylvinylene carbonate, vinylethylene carbonate, 4,4-divinylethylene carbonate, 4,5-divinylethylene carbonate, ethynylethylene carbonate, 4,4-diethynylethylene carbonate, 4,5-diethynylethylene carbonate, propynylethylene carbonate, 4,4-dipropynylethylene carbonate, and 4,5-dipropynylethylene carbonate. Among these compounds, methylphenyl carbonate, ethylphenyl carbonate, diphenyl carbonate, vinylene carbonate, vinylethylene carbonate, 4,4-divinylethylene carbonate, and 4,5-divinylethylene carbonate are particularly preferable.

(Carbonate Compound Having Fluorine Atom)

Examples of the carbonate compound having a fluorine atom include chain carbonates such as methyl trifluoromethyl carbonate, ethyl trifluoromethyl carbonate bis(trifluoromethyl)carbonate, methyl(2,2,2-trifluoroethyl)carbonate, ethyl(2,2,2-trifluoroethyl)carbonate, and bis(2,2,2-trifluoroethyl)carbonate; and cyclic carbonates such as 4-fluoroethylene carbonate, 4.4-difluoroethylene carbonate, 4,5-difluoroethylene, and 4-trifluoromethyl ethylene carbonate. Among these compounds, 4-fluoroethylene carbonate, 4,4-difluoroethylene carbonate, and 4,5-difluoroethylene carbonate are particularly preferable.

(Fluorophosphate Compound)

Examples of the fluorophosphate compound include lithium difluorophosphate, lithium monofluorophosphate, difluorophosphate, monofluorophosphate, methyl difluorophosphate, ethyl difluorophosphate, dimethyl fluorophosphate, and diethyl fluorophosphate. Among these compounds, lithium difluorophosphate and lithium monofluorophosphate are particularly preferable.

(Oxalato Compound)

Examples of the oxalato compound include lithium difluoro(bis(oxalato))phosphate, lithium tetrafluoro(oxalato)phosphate, lithium tris(oxalato)phosphate, lithium difluoro(oxalato)borate, and lithium bisoxalato borate. Among these compounds, lithium difluoro(bis(oxalato))phosphate, lithium tetrafluoro(oxalato)phosphate, and lithium bisoxalato borate are preferable, and lithium difluoro(bis(oxalato))phosphate and lithium bisoxalato borate are particularly preferable.

(Cyclic Sultone Compound)

Examples of the cyclic sultone compound include sultones such as 1,3-propane sultone, 1,4-butane sultone, 1,3-propene sultone, 1-methyl-1,3-propene sultone, 2-methyl-1,3-propene sultone, and 3-methyl-1,3-propene sultone. Among these sultones, 1,3-propane sultone and 1,3-propene sultone are particularly preferable.

(Alicyclic Compound Having Fluorine Atom)

Examples of the alicyclic compound having a fluorine atom include a compound represented by the following formula (VII) or the following formula (VIII).

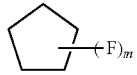

(VII)

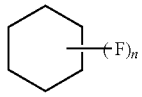

(VIII)

In formula (VII), m is an integer of from 1 to 8; and in formula (VIII), n is an integer of from 1 to 10.

Among the compound represented by formula (VII) or formula (VIII), 1,1,2,2,3,3,4-heptafluorocyclopentane, 1,1,2,2,3,3,4,5-octafluorocyclopentane, 1,2,3,4,5,6-hexafluorocyclohexane, 1,1,2,2,3,4,5,6-octafluorocyclohexane, and 1,1,2,2,3,3,4,4,5,6-decafluorocyclohexane are particularly preferable.

The additive C described above is particularly preferably at least one selected from the group consisting of vinylene carbonate, vinylethylene carbonate, 4-fluoroethylene carbonate, 4,4-difluoroethylene carbonate, 4,5-difluoroethylene carbonate, lithium monofluorophosphate, lithium difluorophosphate, lithium difluorobis(oxalato)phosphate, lithium bisoxalato borate, 1,3-propane sultone, 1,3-propene sultone, and 1,1,2,2,3,3,4-heptafluorocyclopentane.

In the case in which the non-aqueous electrolyte solution of the invention includes the additive C, the included additive C may be only one kind or two or more kinds.

In the case in which the non-aqueous electrolyte solution of the invention includes the additive C, a content thereof (if two or more kinds are included, a total content) is not particularly limited, but is preferably from 0.001 mass % to 10 mass %, more preferably in a range of from 0.05 mass % to 5 mass %, still more preferably in a range of from 0.1 mass % to 4 mass %, still more preferably in a range of from 0.1 mass % to 2 mass %, and particularly preferably in a range of from 0.1 mass % to 1 mass %.

Next will be a description of other components of the non-aqueous electrolyte solution.

Typically, a non-aqueous electrode solution includes an electrolyte and a non-aqueous solvent.

<Non-Aqueous Solvent>

The non-aqueous solvent in the invention can be selected from various known ones. It is preferable to use a cyclic aprotic solvent and/or an acyclic aprotic solvent.

In a case in which improvement in the flash point of solvent is intended to enhance the safety of battery, a cyclic aprotic solvent is preferably used as the non-aqueous solvent.

(Cyclic Aprotic Solvent)

Examples of the cyclic aprotic solvent that can be used include cyclic carbonates, cyclic carboxylic acid esters, cyclic sulfones, and cyclic ethers.

The cyclic aprotic solvent may be used singly or in combination of a plurality of kinds thereof.

The mixing proportion of the cyclic aprotic solvent in the non-aqueous solvent is from 10 mass % to 100 mass %, more preferably from 20 mass % to 90 mass %, and particularly preferably from 30 mass % to 80 mass %. Employing any of such proportions can increase the conductivity of the electrolyte solution that relates to charge-discharge characteristics of battery.

Specific examples of the cyclic carbonates include ethylene carbonate, propylene carbonate, 1,2-butylene carbonate, 2,3-butylene carbonate, 1,2-pentylene carbonate, and 2,3-pentylene carbonate. Among these compounds, ethylene carbonate and propylene carbonate having high dielectric constants are suitably used. In the case of a battery using graphite as a negative electrode active material, ethylene carbonate is more preferable. Additionally, two or more kinds of the cyclic carbonates may be used in mixture.

Specific examples of the cyclic carboxylic acid esters include γ-butyrolactone, δ-valerolactone, and alkyl-substituted forms such as methyl-γ-butyrolactone, ethyl-γ-butyrolactone, and ethyl-δ-valerolactone.

Cyclic carboxylic acid esters have a low vapor pressure, a low viscosity, and a high dielectric constant, and can lower the viscosity of an electrolyte solution without lowering the flash point of the electrolyte solution and the degree of dissociation of an electrolyte. For this reason, cyclic carboxylic acid esters have a feature that the conductivity of the electrolyte solution, which is an index associated with discharge characteristics of battery, can be increased without increasing the inflammability of the electrolyte solution. Thus, in the case in which improvement in the flash point of the solvent is intended, it is preferable to use a cyclic carboxylic acid ester as the cyclic aprotic solvent. Among the cyclic carboxylic acid esters, γ-butyrolactone is most preferable.

Furthermore, preferably, a cyclic carboxylic acid ester is used in mixture with another or other cyclic aprotic solvents. For example, a mixture of a cyclic carboxylic acid ester and a cyclic carbonate and/or an acyclic carbonate may be used.

Examples of the cyclic sulfones include sulfolane, 2-methylsulfolane, 3-methylsulfolane, dimethylsulfone, diethylsulfone, dipropylsulfone, methylethylsulfone, and methylpropylsulfone.

Examples of the cyclic ethers include dioxolane.

(Acyclic Aprotic Solvent)

Examples of the acyclic aprotic solvent that can be used include acyclic carbonates, acyclic carboxylic acid esters, acyclic ethers, and acyclic phosphoric acid esters.

The mixing proportion of the acyclic aprotic solvent in the non-aqueous solvent is from 10 mass % to 100 mass %, more preferably from 20 mass % to 90 mass %, and particularly preferably from 30 mass % to 80 mass %.

Specific examples of the acyclic carbonates include dimethyl carbonate, methyl ethyl carbonate, diethyl carbonate, methyl propyl carbonate, methyl isopropyl carbonate, ethyl propyl carbonate, dipropyl carbonate, methyl butyl carbonate, ethyl butyl carbonate, dibutyl carbonate, methyl pentyl carbonate, ethyl pentyl carbonate, dipentyl carbonate, methyl heptyl carbonate, ethyl heptyl carbonate, diheptyl carbonate, methyl hexyl carbonate, ethyl hexyl carbonate, dihexyl carbonate, methyl octyl carbonate, ethyl octyl carbonate, dioctyl carbonate, and methyl trifluoroethyl carbonate. These acyclic carbonates may be used in mixture of two or more kinds thereof.

Specific examples of the acyclic carboxylic acid esters include methyl pivalate.

Specific examples of the acyclic ethers include dimethoxyethane.

Specific examples of the acyclic phosphoric acid esters include trimethyl phosphate.

(Combination of Solvents)

The non-aqueous solvent used in the non-aqueous electrolyte solution of the invention may be used singly or in combination of a plurality of kinds. In addition, only cyclic aprotic solvents may be used singly or in combination of a plurality of kinds; only acyclic aprotic solvents may be used singly or in combination of a plurality of kinds; or any of mixtures of cyclic aprotic solvents and acyclic aprotic solvents may be used. Particularly, in a case in which improvements in load characteristics and low temperature characteristics of battery are intended, a combination of a cyclic aprotic solvent and an acyclic aprotic solvent is preferably used as the non-aqueous solvent.

Furthermore, in terms of the electrochemical stability of the electrolyte solution, most preferably, a cyclic carbonate is used as the cyclic aprotic solvent and an acyclic carbonate is used as the acyclic aprotic solvent. Additionally, a combination of a cyclic carboxylic acid ester and a cyclic carbonate and/or an acyclic carbonate can also increase the conductivity of the electrolyte solution relating to charge-discharge characteristics of battery.

Specific examples of the combination of a cyclic carbonate and an acyclic carbonate include ethylene carbonate with dimethyl carbonate; ethylene carbonate with methyl ethyl carbonate; ethylene carbonate with diethyl carbonate; propylene carbonate with dimethyl carbonate; propylene carbonate with methyl ethyl carbonate; propylene carbonate with diethyl carbonate; ethylene carbonate with propylene carbonate and methyl ethyl carbonate; ethylene carbonate with propylene carbonate and diethyl carbonate; ethylene carbonate with dimethyl carbonate and methyl ethyl carbonate; ethylene carbonate with dimethyl carbonate and diethyl carbonate; ethylene carbonate with methyl ethyl carbonate, and diethyl carbonate; ethylene carbonate with dimethyl carbonate, methyl ethyl carbonate, and diethyl carbonate; ethylene carbonate with propylene carbonate, dimethyl carbonate, and methyl ethyl carbonate; ethylene carbonate with propylene carbonate, dimethyl carbonate, and diethyl carbonate; ethylene carbonate with propylene carbonate, methyl ethyl carbonate, and diethyl carbonate; and ethylene carbonate with propylene carbonate, dimethyl carbonate, methyl ethyl carbonate, and diethyl carbonate.

The mixing proportion of a cyclic carbonate and an acyclic carbonate is, when expressed as a mass ratio, the ratio of cyclic carbonate:acyclic carbonate is from 5:95 to 80:20, more preferably from 10:90 to 70:30, and particularly preferably from 15:85 to 55:45. When such ratios are employed, an increase in the viscosity of the electrolyte solution is suppressed, and the degree of dissociation of the electrolyte can be increased. Therefore, the conductivity of the electrolyte solution related to the charge-discharge characteristics of a battery can be increased. Furthermore, the solubility of the electrolyte can be further increased. Accordingly, since an electrolyte solution having excellent electrical conductivity at normal temperature or at a low temperature can be obtained, the rate characteristics of a battery at normal temperature to a low temperature can be improved.

Specific examples of the combination of a cyclic carboxylic acid ester and a cyclic carbonate and/or an acyclic carbonate include γ-butyrolactone with ethylene carbonate; γ-butyrolactone with ethylene carbonate and dimethyl carbonate; γ-butyrolactone with ethylene carbonate and methyl ethyl carbonate; γ-butyrolactone with ethylene carbonate and diethyl carbonate; γ-butyrolactone with propylene carbonate; γ-butyrolactone with propylene carbonate and dimethyl carbonate; γ-butyrolactone with propylene carbonate and methyl ethyl carbonate; γ-butyrolactone with propylene carbonate and diethyl carbonate; γ-butyrolactone with ethylene carbonate and propylene carbonate; γ-butyrolactone with ethylene carbonate, propylene carbonate, and dimethyl carbonate; γ-butyrolactone with ethylene carbonate, propylene carbonate, and methyl ethyl carbonate; γ-butyrolactone with ethylene carbonate, propylene carbonate, and diethyl carbonate; γ-butyrolactone with ethylene carbonate, dimethyl carbonate, and methyl ethyl carbonate; γ-butyrolactone with ethylene carbonate, dimethyl carbonate, and diethyl carbonate; γ-butyrolactone with ethylene carbonate, methyl ethyl carbonate, and diethyl carbonate; γ-butyrolactone with ethylene carbonate, dimethyl carbonate, methyl ethyl carbonate, and diethyl carbonate; γ-butyrolactone with ethylene carbonate, propylene carbonate, dimethyl carbonate, and methyl ethyl carbonate; γ-butyrolactone with ethylene carbonate, propylene carbonate, dimethyl carbonate, and diethyl carbonate; γ-butyrolactone with ethylene carbonate, propylene carbonate, methyl ethyl carbonate, and diethyl carbonate; γ-butyrolactone with ethylene carbonate, propylene carbonate, dimethyl carbonate, methyl ethyl carbonate, and diethyl carbonate; γ-butyrolactone with sulfolane; γ-butyrolactone with ethylene carbonate and sulfolane; γ-butyrolactone with propylene carbonate and sulfolane; γ-butyrolactone with ethylene carbonate, propylene carbonate, and sulfolane; and γ-butyrolactone with sulfolane and dimethyl carbonate.

(Other Solvent)

The non-aqueous electrolyte solution according to the invention may also include another solvent in addition to the solvents described above, as the non-aqueous solvent. Specific examples of the other solvent include amides such as dimethylformamide; acyclic carbamates such as methyl-N,N-dimethyl carbamate; cyclic amides such as N-methylpyrrolidone; cyclic ureas such as N,N-dimethylimidazolidinone; boron compounds such as trimethyl borate, triethyl borate, tributyl borate, trioctyl borate, and trimethylsilyl borate; and polyethylene glycol derivatives represented by the following formulae:

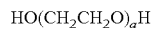

$$HO(CH_2CH_2O)_aH$$

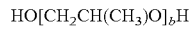

$$HO[CH_2CH(CH_3)O]_bH$$

$$CH_3O(CH_2CH_2O)_cH$$

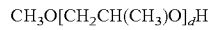

$$CH_3O[CH_2CH(CH_3)O]_dH$$

$CH_3O(CH_2CH_2O)_eCH_3$ $CH_3O[CH_2CH(CH_3)O]_fCH_3$ $C_9H_{19}PhO(CH_2CH_2O)_g[CH(CH_3)O]_hCH_3$ (Ph represents a phenyl group)

$CH_3O[CH_2CH(CH_3)O]_iCO[OCH(CH_3)CH_2]_jOCH_3$

In the above formulae, a to f each represent an integer of from 5 to 250; g to j each represent an integer of from 2 to 249; 5≤g+h≤250; and 5≤i+j≤250.

<Electrolyte>

In the non-aqueous electrolyte solution of the invention, various electrolytes can be used, and usually, any electrolyte which is used as an electrolyte for non-aqueous electrolyte solutions can be used.

Specific examples of the electrolyte in the invention include tetraalkylammonium salts such as $(C_2H_5)_4NPF_6$, $(C_2H_5)_4NBF_4$, $(C_2H_5)_4NClO_4$, $(C_2H_5)_4NAsF_6$, $(C_2H_5)_4N_2SiF_6$, $(C_2H_5)_4NOSO_2C_kF_{(2k+1)}$ (k=an integer of from 1 to 8), and $(C_2H_5)_4NPF_n[C_kF_{(2k+1)}]_{(6-n)}$ (n=an integer of from 1 to 5, and k=an integer of from 1 to 8); and lithium salts such as $LiPF_6$, $LiBF_4$, $LiClO_4$, $LiAsF_6$, $Li_2SiF_6$, $LiOSO_2C_kF_{(2k+1)}$ (k=an integer of from 1 to 8), and $LiPF_n[C_kF_{(2k+1)}]_{(6-n)}$ (n=an integer of from 1 to 5, and k=an integer of from 1 to 8). Furthermore, lithium salts represented by the following formulae can also be used:

$LiC(SO_2R^{27})(SO_2R^{28})(SO_2R^{29})$, $LiN(SO_2OR^{30})(SO_2OR^{31})$, and $LiN(SO_2R^{32})(SO_2R^{33})$ (where $R^{27}$ to $R^{33}$ may be identical with or different from each other, and each represent a perfluoroalkyl group having from 1 to 8 carbon atoms). These electrolytes may be used singly or in mixture of two or more kinds.

Among these compounds, lithium salts are particularly preferable, and $LiPF_6$, $LiBF_4$, $LiOSO_2C_kF_{(2k+1)}$ (k=an integer of from 1 to 8), $LiClO_4$, $LiAsF_6$, $LiNSO_2[C_kF_{(2k+1)}]_2$ (k=an integer of from 1 to 8), and $LiPF_n[C_kF_{(2k+1)}]_{(6-n)}$ (n=an integer of from 1 to 5, and k=an integer of from 1 to 8) are more preferable.

The electrolyte according to the invention is included at a concentration of usually from 0.1 mol/L to 3 mol/L, and preferably from 0.5 mol/L to 2 mol/L in the non-aqueous electrolyte solution.

In the non-aqueous electrolyte solution of the invention, in the case in which a cyclic carboxylic acid ester such as γ-butyrolactone is used in combination as the non-aqueous solvent, the non-aqueous electrolyte solution particularly preferably includes $LiPF_6$. Since $LiPF_6$ has a high degree of dissociation and therefore can increase the conductivity of the electrolyte solution, and also acts to suppress the reductive decomposition reaction of the electrolyte solution on the negative electrode. $LiPF_6$ may be used singly, or may be used together with an electrolyte other than $LiPF_6$. As for the other electrolyte, any electrolyte which is usually used as an electrolyte for non-aqueous electrolyte solution can be used. As for the other electrolyte, among the specific examples of lithium salts described above, a lithium salt other than $LiPF_6$ is preferable.

Specific examples include: $LiPF_6$ with $LiBF_4$; $LiPF_6$ with $LiN[SO_2C_kF_{(2k+1)}]_2$ (k=an integer of from 1 to 8); $LiPF_6$ with $LiBF_4$; and $LiN[SO_2C_kF_{(2k+1)}]$ (k=an integer of from 1 to 8).

The proportion of $LiPF_6$ included in the lithium salts is from 1 mass % to 100 mass %, preferably from 10 mass % to 100 mass %, and more preferably from 50 mass % to 100 mass %. Such an electrolyte is included at a concentration of from 0.1 mol/L to 3 mol/L, and preferably from 0.5 mol/L to 2 mol/L in the non-aqueous electrolyte solution.

The non-aqueous electrolyte solution of the invention may include at least one compound other than the above-described compounds, as an additive, in a range that does not impair the object of the invention.

Specific examples of the other compound include sulfates such as dimethyl sulfate, diethyl sulfate, ethylene sulfate, propylene sulfate, butene sulfate, pentene sulfate, and vinylene sulfate; and sulphur compounds such as sulfolane, 3-sulfolene, and divinyl sulfone.

These compounds may be used singly or in combination of two or more kinds thereof.

Among these compounds, ethylene sulfate, propylene sulfate, butene sulfate, and pentene sulfate are preferable.

The non-aqueous electrolyte solution of the invention is not only suitable as a non-aqueous electrolyte solution for a lithium secondary battery, but can also be used as a non-aqueous electrolyte solution for a primary battery, a non-aqueous electrolyte solution for a electrochemical capacitor, or a non-aqueous electrolyte solution for an electric double layer capacitor or an aluminum electrolytic capacitor.

[Lithium Secondary Battery]

A lithium secondary battery of the invention is configured by including a negative electrode, a positive electrode, and the non-aqueous electrolyte solution of the invention.

Usually, a separator is provided between the negative electrode and the positive electrode.

(Negative Electrode)

As the negative electrode active material that constitutes the negative electrode, at least one selected from the group consisting of metal lithium, lithium-containing alloys, metals or alloys capable of alloying with lithium, oxides capable of doping and dedoping lithium ions, transition metal nitrides capable of doping and dedoping lithium ions, and carbon materials capable of doping and dedoping lithium ions (these may be used singly, or any of mixtures including two or more kinds thereof may be used) can be used.

Examples of the metals or alloys capable of alloying with lithium (or lithium ions) include silicon, silicon alloys, tin, and tin alloys. Alternatively, lithium titanate may be used.

Among these compounds, a carbon material capable of doping and dedoping lithium ions is preferable. Examples of such a carbon material include carbon black, activated carbon, a graphite material (artificial graphite or natural graphite), and an amorphous carbon material. The form of the carbon material may be any of a fibrous form, a spherical form, a potato form and a flake form.

Specific examples of the amorphous carbon material include hard carbon, cokes, mesocarbon microbeads (MCMB) calcined at or below 1500° C., and mesophase pitch-based carbon fibers (MCF).

Examples of the graphite material include natural graphite and artificial graphite. Examples of the artificial graphite to be used include graphitized MCMB and graphitized MCF. Furthermore, examples of the graphite material that can be used include boron-containing graphites. Additional examples of the graphite material that can be used include a graphite material coated with a metal such as gold, platinum, silver, copper or tin, a graphite material coated with an amorphous carbon, and a mixture of amorphous carbon and graphite.

These carbon materials may be used singly or in mixture of two or more kinds thereof. The carbon material is particularly preferably a carbon material whose interplanar spacing d(002) of the (002) plane measured by an X-ray analysis is 0.340 nm or less. Furthermore, the carbon material is also preferably a graphite having a true density of 1.70 g/cm$^3$ or greater or a highly crystalline carbon material having properties close thereto. The use of any of the carbon materials as described above can further increase the energy density of the battery.

(Positive Electrode)

Examples of the positive electrode active material that constitutes the positive electrode include transition metal oxides or transition metal sulfides, such as $MoS_2$, $TiS_2$, $MnO_2$, and $V_2O_5$; composite oxides composed of lithium and transition metals, such as $LiCoO_2$, $LiMnO_2$, $LiMn_2O_4$, $LiNiO_2$, $LiNi_xCo_{(1-x)}O_2$ [0<X<1], $Li_{1+\alpha}Mc_{1-\alpha}O_2$ (Mc is a transition metal element including Mn, Ni, and Co; $1.0 \leq (1+\alpha)/(1-\alpha) \leq 1.6$) having an $\alpha$-NaFeO$_2$ type crystal structure, $LiNi_xCo_yMn_zO_2$[x+y+z=1; 0<x<1; 0<y<1; 0<z<1] (for example, $LiNi_{0.33}Co_{0.33}Mn_{0.33}O_2$, $LiNi_{0.5}Co_{0.2}Mn_{0.3}O_2$, etc.), $LiFePO_4$, and $LiMnPO_4$; and electroconductive polymer materials such as polyaniline, polythiophene, polypyrrole, polyacetylene, polyacene, dimercaptothiadiazole, and polyaniline composites. Among these materials, composite oxides composed of lithium and transition metals are particularly preferable. When the negative electrode is made of a lithium metal or a lithium alloy, a carbon material can be used as the positive electrode. Additionally, a mixture of a composite oxide of lithium and a transition metal with a carbon material can be used as the positive electrode.

The positive electrode active materials described above may be used singly or in combination of two or more kinds thereof. If the positive electrode active material has insufficient electroconductivity, the positive electrode can be constructed by using the positive electrode active material together with an electroconductive aid. Examples of the electroconductive aid include carbon materials such as carbon black, amorphous whisker, and graphite.

(Separator)

The separator is a film which electrically insulates the positive electrode and the negative electrode, and transmits lithium ions, and examples thereof include a porous film and a polymer electrolyte.

A finely porous polymer film is suitably used as the porous film, and examples of materials of the porous film include polyolefins, polyimides, polyvinylidene fluoride, and polyesters.

Particularly, porous polyolefins are preferable, and specific examples thereof include a porous polyethylene film, a porous polypropylene film, and a multilayer film composed of a porous polyethylene film and a porous polypropylene film. The porous polyolefin film may be coated with another resin excellent in thermal stability.

Examples of the polymer electrolyte include a polymer containing a dissolved lithium salt and a polymer swollen with an electrolyte solution.

The non-aqueous electrolyte solution of the invention may also be used to swell a polymer to obtain a polymer electrolyte.

(Configuration of Battery)

The lithium secondary battery of the invention includes the negative electrode active material, the positive electrode active material, and the separator described above.

The lithium secondary battery of the invention can be formed in any of various known shapes and can be formed into a cylindrical shape, a coin shape, a rectangular shape, a film shape, and any other optional shape. However, the basic structure of the battery is the same irrespective of the shape thereof, and design modifications can be made according to purpose.

An example of the lithium secondary battery (the non-aqueous electrolyte solution secondary battery) of the invention may be a coin battery as illustrated in FIG. 1.

In the coin battery illustrated in FIG. 1, a disc-shaped negative electrode 2, a separator 5 in which the non-aqueous electrolyte solution is injected, a disc-shaped positive electrode 1, and as needed, spacer plates 7 and 8 made of stainless steel, aluminum or the like are laminated in this order, and, in the laminated state, are accommodated between a positive electrode can 3 (hereinafter also referred to as a "battery can") and a sealing plate 4 (hereinafter also referred to as a "battery can lid"). The positive electrode can 3 and the sealing plate 4 are sealed by caulking with a gasket 6.

In this example, the non-aqueous electrolyte solution of the invention can be used as the non-aqueous electrolyte solution to be injected into the separator 5.

The lithium secondary battery of the invention may be a lithium secondary battery obtained by charging and discharging a lithium secondary battery (a lithium secondary battery before charge and discharge) that includes a negative electrode, a positive electrode, and the non-aqueous electrolyte solution of the invention.

Specifically, the lithium secondary battery of the invention may be a lithium secondary battery (a lithium secondary battery that has been charged and discharged) obtained by first producing a lithium secondary battery before charge and discharge that includes a negative electrode, a positive electrode and the non-aqueous electrolyte solution of the invention and subsequently charging and discharging the lithium secondary battery before charge and discharge one or more times.

There are no particular limitations on the use of the lithium secondary battery, and it can be used in various known applications. For example, the lithium secondary battery can be widely utilized in small-sized portable devices as well as in large-sized devices, such as notebook computers, mobile computers, mobile telephones, headphone stereos, video movie cameras, liquid crystal television sets, handy cleaners, electronic organizers, calculators, radios, back-up power supply applications, motors, automobiles, electric cars, motorcycles, electric motorcycles, bicycles, electric bicycles, illuminating devices, game players, time pieces, electric tools, and cameras.

EXAMPLES

Hereinafter, the invention will be described more specifically by way of Examples. However, the invention is not limited thereto.

In the following Examples, "wt %" represents mass %.

In addition, in the following Examples, "addition amount" represents a content in a non-aqueous electrolyte solution to be finally obtained.

Example 1

A lithium secondary battery was produced by the following procedure.

<Production of Negative Electrode>

20 parts by mass of artificial graphite, 80 parts by mass of natural graphite-based graphite, 1 part by mass of carboxymethyl cellulose, and 2 parts by mass of a SBR latex were kneaded in water solvent, and thus a negative electrode mixture slurry in a paste form was prepared.

Next, this negative electrode mixture slurry was applied on a strip-shaped negative electrode current collector made of a copper foil having a thickness of 18 μm, and the slurry was dried. Subsequently, the assembly was compressed with a roll press, and thus a sheet-like negative electrode composed of a negative electrode current collector and a negative electrode active material layer was obtained. The coating density of the negative electrode active material layer was 10 mg/cm$^2$, and the packing density was 1.5 g/ml.

<Production of Positive Electrode>

90 parts by mass of LiCoO$_2$, 5 parts by mass of acetylene black, and 5 parts by mass of polyvinylidene fluoride were kneaded in N-methylpyrrolidinone as a solvent, and thus a positive electrode mixture slurry in a paste form was prepared.

Next, this positive electrode mixture slurry was applied on a strip-shaped positive electrode current collector made of an aluminum foil having a thickness of 20 μm, and the slurry was dried. Subsequently, the assembly was compressed with a roll press, and thus a sheet-like positive electrode composed of a positive electrode current collector and a positive electrode active material layer was obtained. The coating density of the positive electrode active material layer was 30 mg/cm$^2$, and the packing density was 2.5 g/ml.

<Preparation of Non-Aqueous Electrolyte Solution>

Ethylene carbonate (EC), dimethyl carbonate (DMC), and methyl ethyl carbonate (EMC) were mixed together in a proportion of 30:35:35 (mass ratio) to obtain a mixed solvent as a non-aqueous solvent. LiPF$_6$ as an electrolyte was dissolved in the obtained mixed solvent such that the concentration of the electrolyte in a non-aqueous electrolyte solution to be finally obtained was 1 mol/liter.

To the solution thus obtained, the above exemplary compound 1 as the additive A (addition amount: 0.5 wt %) and cyclohexylbenzene as the additive B (addition amount: 2 wt %) were respectively added to obtain a non-aqueous electrolyte solution.

<Production of Coin Battery>

The negative electrode described above was punched into a disc form having a diameter of 14 mm, while the positive electrode described above was punched into a disc form having a diameter of 13 mm, and thus coin-shaped electrodes (a negative electrode and a positive electrode) were obtained. Furthermore, a microporous polyethylene film having a thickness of 20 μm was punched into a disc form having a diameter of 17 mm, and thus a separator was obtained.

The coin-shaped negative electrode, the separator and the coin-shaped positive electrode thus obtained were laminated in this order inside a battery can (size 2032) made of stainless steel, and 20 μl of the non-aqueous electrolyte solution was injected therein to impregnate the separator, the positive electrode, and the negative electrode.

Furthermore, an aluminum plate (thickness: 1.2 mm, diameter: 16 mm) and a spring were mounted on the positive electrode, a gasket made of polypropylene was inserted, and the battery was sealed by caulking with the battery can lid. Thus, a coin type lithium secondary battery (hereinafter, may be referred to as a test battery) having a diameter of 20 mm and a height of 3.2 mm and having the configuration illustrated in FIG. 1 was prepared.

The coin battery (a test battery) thus obtained was subjected to the following measurements.

[Evaluation Method]

<Resistance Characteristics of Battery: Measurement of Initial Battery Resistance>

The coin battery was charged at a constant voltage of 4.2 V. Next, the charged coin battery was cooled to −20° C. in a constant temperature chamber and discharged at −20° C. at a constant current of 0.2 mA to measure a potential decrease for 10 seconds from the start of discharging, thereby measuring the direct current resistance [Ω] (−20° C.) of the coin battery. The obtained value was used as an initial resistance value [Ω] (−20° C.).

The initial resistance value [Ω] (−20° C.) of a coin battery of Comparative Example 1 to be described later was also measured in the same manner.

From these results, "an initial battery resistance [%]" was obtained as an initial resistance value (a relative value; %) of Example 1 with respect to the initial resistance value [Ω] (−20° C.) of Comparative Example 1 defined as 100%, by the following formula.

Table 1 shows the obtained results.

Initial battery resistance [%]=(initial resistance value [Ω] of Example 1/initial resistance value [Ω] of Comparative Example 1)×100[%]

<Resistance Characteristics of Battery: Measurement of Post-Storage Battery Resistance>

The coin battery was charged at a constant voltage of 4.2 V. Next, the charged coin battery was stored in a constant temperature chamber at 80° C. for 2 days, and then the direct current resistance [Ω] (−20° C.) of the coin battery was measured in the same manner as the initial battery resistance. The obtained value was used as a post-storage resistance value [Ω] (−20° C.).

The initial resistance value [Ω] (−20° C.) of a coin battery of Comparative Example 1 to be described later was also measured in the same manner.

From these results, "a post-storage battery resistance [%]" was obtained as a post-storage resistance value (a relative value %) of Example 1 with respect to the post-storage resistance value [Ω] (−20° C.) of Comparative Example 1 defined as 100%, by the following formula.

Table 1 shows the obtained results.

Post-storage battery resistance [%]=(post-storage resistance value [Ω] of Example 1/post-storage resistance value [Ω] of Comparative Example 1)×100[%]

Examples 2 to 27 and Comparative Examples 1 to 10

The same operation as in Example 1 was performed except that at least one of the kind of the additive A, the addition amount of the additive A, the kind of the additive B, the addition amount of the additive B, the kind of the additive C, and the addition amount of the additive C was changed as shown in the following Table 1. Table 1 below shows the results.

In Table 1, the symbol "-" in the columns of the additives A, B, and C indicates no addition of the additives.

For example, Comparative Example 1 is an Example in which none of the additives A, B, and C were added.

TABLE 1

| | Additive in non-aqueous electrolyte solution | | | Battery resistance characteristics (−20° C.) | |
|---|---|---|---|---|---|
| | Additive A (Addition amount) | Additive B (Addition amount) | Additive C (Addition amount) | Initial (%) | Post-storage (%) |
| Comparative Example 1 | — | — | — | 100 | 100 |
| Comparative Example 2 | Exemplary compound 1 | — | — | 113 | 94 |
| Example 1 | (0.5 wt %) | Cyclohexylbenzene (2 wt %) | — | 99 | 81 |
| Example 2 | | Fluorobenzene (2 wt %) | — | 95 | 81 |
| Example 3 | | Fluorobenzene (10 wt %) | — | 98 | 84 |
| Example 4 | | 2-fluorotoluene (2 wt %) | — | 97 | 79 |
| Example 5 | | 2-fluorobiphenyl (2 wt %) | — | 98 | 82 |
| Example 6 | | N-methyloxazolidinone (2 wt %) | — | 98 | 81 |
| Example 7 | | Cyclohexylbenzene (2 wt %) | Lithium difluorophosphate (0.5 wt %) | 97 | 78 |
| Example 8 | | 2-fluorotoluene (2 wt %) | Lithium difluorophosphate (0.5 wt %) | 95 | 79 |
| Example 9 | | 2-fluorotoluene (2 wt %) | Vinylene carbonate (0.5 wt %) | 97 | 81 |
| Example 10 | | N-methyloxazolidinone (2 wt %) | Lithium difluorophosphate (0.5 wt %) | 95 | 80 |
| Comparative Example 3 | Exemplary compound 22 | — | — | 77 | 92 |
| Example 11 | (0.5 wt %) | Cyclohexylbenzene (2 wt %) | — | 71 | 78 |
| Example 12 | | Fluorobenzene (2 wt %) | — | 70 | 76 |
| Example 13 | | Fluorobenzene (10 wt %) | — | 73 | 78 |
| Example 14 | | 2-fluorotoluene (2 wt %) | — | 68 | 79 |
| Example 15 | | 2-fluorotoluene (5 wt %) | — | 68 | 79 |
| Example 16 | | 2-fluorobiphenyl (2 wt %) | — | 69 | 77 |
| Example 17 | | N-methyloxazolidinone (2 wt %) | — | 68 | 73 |
| Example 18 | | N-methyloxazolidinone (5 wt %) | — | 68 | 78 |
| Example 19 | | Cyclohexylbenzene (2 wt %) | Lithium difluorophosphate (0.5 wt %) | 69 | 72 |
| Example 20 | | 2-fluorotoluene (2 wt %) | Lithium difluorophosphate (0.5 wt %) | 68 | 78 |
| Example 21 | | 2-fluorotoluene (2 wt %) | Vinylene carbonate (0.5 wt %) | 70 | 80 |
| Example 22 | | N-methyloxazolidinone (2 wt %) | Lithium difluorophosphate (0.5 wt %) | 68 | 75 |
| Example 23 | Exemplary compound 22 (1 wt %) | Cyclohexylbenzene (2 wt %) | — | 68 | 77 |
| Example 24 | | 2-fluorotoluene (2 wt %) | — | 68 | 78 |
| Example 25 | Exemplary compound 22 (2 wt %) | Cyclohexylbenzene (2 wt %) | — | 70 | 76 |
| Example 26 | | 2-fluorotoluene (2 wt %) | — | 70 | 78 |
| Example 27 | | N-methyloxazolidinone (2 wt %) | — | 68 | 78 |
| Comparative Example 4 | Exemplary compound 1 (2.5 wt %) | — | — | 138 | 91 |
| Comparative Example 5 | Exemplary compound 22 (2.5 wt %) | — | — | 93 | 106 |
| Comparative Example 6 | — | Cyclohexylbenzene (2.5 wt %) | — | 104 | 82 |
| Comparative Example 7 | — | Fluorobenzene (2.5 wt %) | — | 102 | 95 |
| Comparative Example 8 | — | 2-fluorotoluene (2.5 wt %) | — | 100 | 103 |

TABLE 1-continued

| | Additive in non-aqueous electrolyte solution | | | Battery resistance characteristics (−20° C.) | |
|---|---|---|---|---|---|
| | Additive A (Addition amount) | Additive B (Addition amount) | Additive C (Addition amount) | Initial (%) | Post-storage (%) |
| Comparative Example 9 | — | 2-fluorobiphenyl (2.5 wt %) | — | 100 | 96 |
| Comparative Example 10 | — | N-methyloxazolidinone (2.5 wt %) | — | 111 | 120 |

—Explanation of Table 1—

Exemplary compounds 1 and 22 are specific examples of the additive A (specifically, a cyclic sulfate compound represented by formula (I)).

Cyclobenzene, fluorobenzene, 2-fluorotoluene, and 2-fluorobiphenyl are specific examples of the additive B (specifically, an aromatic compound substituted with at least one of a halogen atom or an alkyl group).

N-methyloxazolidinone is a specific example of the additive B (specifically, a carbamate compound).

Lithium difluorophosphate is a specific example of the additive C (specifically, a fluorophosphate compound).

Vinylene carbonate is a specific example of the additive C (specifically, a carbonate compound having a carbon-carbon unsaturated bond).

Results shown in Table 1 have verified that the use of the non-aqueous electrolyte solution for a battery including the additive A and the additive B can significantly reduce initial (pre-storage) and post-storage battery resistances (i.e., improve resistance characteristics).

The entire disclosure of Japanese Patent Application No. 2013-198670 filed on Sep. 25, 2013 is incorporated herein by reference.

All publications, patent applications, and technical standards mentioned in this specification are incorporated herein by reference to the same extent as if each individual publication, patent application, or technical standard was specifically and individually indicated to be incorporated by reference.

The invention claimed is:

1. A non-aqueous electrolyte solution for a battery, comprising:

an additive A which is a cyclic sulfate compound represented by the following formula (I):

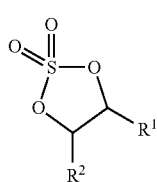

wherein, in formula (I), $R^2$ represents a hydrogen atom, and $R^1$ represents a group represented by formula (II) or a group represented by formula (III):

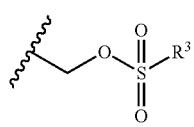

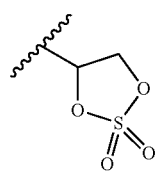

wherein, in formula (II), $R^3$ represents a methyl group; and wavy lines in formula (II) and formula (III) represent bonding positions; and an additive B which is at least one selected from the group consisting of benzene or biphenyl substituted with at least one selected from the group consisting of a fluorine atom, a methyl group, and a cyclohexyl group, and a cyclic carbamate compound represented by the following formula (V):

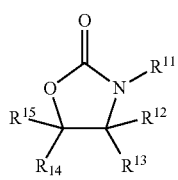

wherein, in formula (V), $R^{11}$ represents a methyl group, and $R^{12}$ to $R^{15}$ each represent a hydrogen atom.

2. The non-aqueous electrolyte solution for a battery according to claim 1, further comprising an additive C which is at least one selected from the group consisting of a carbonate compound having a carbon-carbon unsaturated bond, a carbonate compound having a fluorine atom, a fluorophosphate compound, an oxalato compound, a cyclic sultone compound, and an alicyclic compound having a fluorine atom.

3. The non-aqueous electrolyte solution for a battery according to claim 2, wherein the additive C is at least one selected from the group consisting of vinylene carbonate, vinylethylene carbonate, 4-fluoroethylene carbonate, 4,4-difluoroethylene carbonate, 4,5-difluoroethylene carbonate, lithium monofluorophosphate, lithium difluorophosphate, lithium difluorobis(oxalato)phosphate, lithium bisoxalato borate, 1,3-propane sultone, 1,3-propene sultone, and 1,1,2,2,3,3,4-heptafluorocyclopentane.

4. The non-aqueous electrolyte solution for a battery according to claim 2, wherein a content of the additive C is from 0.001 mass % to 10 mass % with respect to a total amount of the non-aqueous electrolyte solution for a battery.

5. The non-aqueous electrolyte solution for a battery according to claim 1, wherein a content of the additive A is from 0.001 mass % to 10 mass % with respect to a total amount of the non-aqueous electrolyte solution for a battery.

6. The non-aqueous electrolyte solution for a battery according to claim 1, wherein a content of the additive B is from 0.001 mass % to 20 mass % with respect to a total amount of the non-aqueous electrolyte solution for a battery.

7. The non-aqueous electrolyte solution for a battery according to claim 1, wherein a content of the additive A is from 0.001 mass % to 10 mass % with respect to a total amount of the non-aqueous electrolyte solution for a battery, and a content of the additive B is from 0.001 mass % to 20 mass % with respect to the total amount of the non-aqueous electrolyte solution for a battery.

8. The non-aqueous electrolyte solution for a battery according to claim 1, wherein a content mass ratio of the additive B to the additive A (additive B/additive A) is from 1.0 to 20.0.

9. A lithium secondary battery comprising a positive electrode; a negative electrode including, as a negative electrode active material, at least one selected from the group consisting of metal lithium, a lithium-containing alloy, a metal or alloy capable of alloying with lithium, an oxide capable of doping and dedoping lithium ions, a transition metal nitride capable of doping and dedoping lithium ions, and a carbon material capable of doping and dedoping lithium ions; and the non-aqueous electrolyte solution for a battery according to claim 1.

10. A lithium secondary battery obtained by charging and discharging a lithium secondary battery comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping lithium ions, a transition metal nitride capable of doping and dedoping lithium ions, and a carbon material capable of doping and dedoping lithium ions; and the non-aqueous electrolyte solution for a battery according to claim 1.

* * * * *